(12) United States Patent
Fuhrman et al.

(10) Patent No.: US 7,503,325 B2
(45) Date of Patent: Mar. 17, 2009

(54) DEVICE AND METHOD OF PARTIALLY SEPARATING GAS

(75) Inventors: Bradley P. Fuhrman, Buffalo, NY (US); Mark S. Dowhy, Buffalo, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 193 days.

(21) Appl. No.: 10/955,989

(22) Filed: Sep. 30, 2004

(65) Prior Publication Data

US 2005/0076911 A1    Apr. 14, 2005

Related U.S. Application Data

(60) Provisional application No. 60/507,902, filed on Sep. 30, 2003.

(51) Int. Cl.
A61M 16/00 (2006.01)
A61M 11/00 (2006.01)
A61M 15/00 (2006.01)
A62B 7/00 (2006.01)
A62B 9/00 (2006.01)
A62B 18/00 (2006.01)

(52) U.S. Cl. ............................. 128/204.18; 128/200.14; 128/200.24

(58) Field of Classification Search ................ 128/200.14–200.24, 203.12–203.21, 203.23–203.25, 128/204.14, 204.18, 207.14–207.18
See application file for complete search history.

(56) References Cited

U.S. PATENT DOCUMENTS

| 3,938,551 | A | | 2/1976 | Henkin |
| 4,060,078 | A | * | 11/1977 | Bird ........................ 128/204.25 |
| 4,442,856 | A | * | 4/1984 | Betz ............................. 137/98 |
| 5,810,002 | A | | 9/1998 | Dittmann |
| 5,823,184 | A | | 10/1998 | Gross |
| 5,979,443 | A | | 11/1999 | Dingley |
| 5,983,896 | A | | 11/1999 | Fukunaga et al. |
| 6,003,511 | A | | 12/1999 | Fukunaga et al. |
| 6,095,137 | A | * | 8/2000 | Wallroth et al. ......... 128/203.26 |
| 6,098,622 | A | | 8/2000 | Nobile et al. |
| 6,123,674 | A | | 9/2000 | Rich |
| 6,192,884 | B1 | | 2/2001 | Vann et al. |
| 6,340,023 | B2 | * | 1/2002 | Elkins .................... 128/200.21 |
| 6,439,231 | B1 | | 8/2002 | Fukunaga et al. |
| 6,575,164 | B1 | | 6/2003 | Jaffe et al. |
| 6,675,799 | B2 | | 1/2004 | Fuhrman et al. |
| 6,948,493 | B2 | * | 9/2005 | Dunlop .................. 128/203.12 |
| 2002/0157663 | A1 | * | 10/2002 | Blacker et al. .......... 128/200.21 |
| 2003/0127096 | A1 | * | 7/2003 | McAuliffe et al. ....... 128/204.18 |
| 2005/0029192 | A1 | * | 2/2005 | Arnold et al. ................ 210/641 |

FOREIGN PATENT DOCUMENTS

WO    WO 99/62581    12/1999
WO    WO 03/026721 A3    4/2003

* cited by examiner

Primary Examiner—Justine R Yu
Assistant Examiner—Kristen C Matter
(74) Attorney, Agent, or Firm—Hodgson Russ LLP

(57) ABSTRACT

The invention includes a partial gas separator, which may include a housing and a movable divider in the housing. A method according to the invention may provide a partial gas separator and gas may be moved to or from the housing. While moving gas to or from the housing, the movable divider may be allowed to move with the flow of gas.

19 Claims, 14 Drawing Sheets

DEVICE AND METHOD OF PARTIALLY SEPARATING GAS

CROSS-REFERENCE TO RELATED APPLICATION

This application claims the benefit of priority to U.S. provisional patent application Ser. No. 60/507,902, filed on Sep. 30, 2003.

FIELD OF THE INVENTION

The present invention relates to devices and methods for ventilating a patient.

BACKGROUND OF THE INVENTION

Rebreathing circuits make it possible to reduce the amount of fresh gas delivered to a patient's lungs without raising blood carbon dioxide concentration. The reduction of fresh gas flow, in turn, conserves inhalational therapeutic agents. An example of this is the use of a rebreathing circuit to deliver volatile anesthesia. Other potential uses of rebreathing circuits include: efficient delivery of inhalational nitric oxide for pulmonary vasodilation, administration of helium gas as a means to reduce resistance to turbulent air flow in large airways, and reducing fresh gas flow as a means to limit evaporation of perfluorocarbon liquid from the lungs during partial liquid ventilation. Rebreathing circuits may also be used to enhance the delivery of aerosolized therapeutic agents.

Rebreathing circuits are designed primarily to support anesthetic administration. In anesthesia applications, the gas in the rebreathing circuit is kept separate from the gas used to mechanically pressurize the respiratory circuit and thereby move the lungs. Were this separation to be incomplete or only partial, mixing of the gas steams might dilute the anesthetic being administered, which could result in the patient waking during surgery.

The prior art includes U.S. Pat. No. 4,989,597, which discloses a means to directly interface a ventilator to an anesthesia re-breathing circuit comprising a long, convoluted tube having a narrow diameter, yet large total volume. Such a device allows mixing of ventilator and re-breather gas streams. Under conditions of constant tidal volume, such a device causes a steady fractional admixture of the gas columns. Appropriate anesthetic concentration in the re-breather is maintained by delivery of an excess of anesthetic to the re-breather as compensation for losses due to mixing with the ventilator gas column. In that system, there is no divider between the separated gas columns. Instead there is an "open separation" of the gases resulting from the long mixing tube, which may contain two to three liters of gas.

SUMMARY OF THE INVENTION

The invention includes a gas separator. Such a gas separator may include (a) a housing, having an inner surface, a first orifice in pneumatic communication with a patient, and a second orifice in pneumatic communication with a supply of gas; (b) a movable divider in the housing, the movable divider having a first side, a second side and an edge between the first and second sides, the edge being positioned proximate to the inner surface of the housing to limit, but not prevent, the movement of gas from one of the sides to the other side, and (c) a guide in the housing, the guide being associated with the movable divider so as to allow the movable divider to move toward the first orifice during inhalation and toward the second orifice during exhalation, and being associated with the movable divider so as to keep the edge proximate to the inner surface of the housing.

A method according to the invention may provide a partial gas separator like the one described in the immediately preceding paragraph. Gas may be moved from the housing. While moving gas from the housing, the movable divider may be allowed to travel toward the first orifice, and a limited amount of gas may be allowed to move from the second side to the first side. For non-anesthetic rebreathing applications, some mixing of the gas streams would be inconsequential.

Although the invention is not limited to devices and methods that partially separate a mechanical ventilator or fresh gas source from a rebreathing circuit, the invention is illustrated from time to time by describing such a device and/or method. The invention may be used to provide an interface, which partially separates a mechanical ventilator or fresh gas source from a rebreathing circuit. The invention may be used to facilitate the administration of inhalational therapeutic agents. In this implementation of the invention, both gas streams (that of the ventilator or supplemental gas source, and that of the rebreathing circuit) may move in the same direction during inspiration, that being toward the patient. During expiration, both gas streams may move in the same direction, that being toward the ventilator or supplemental gas source.

BRIEF DESCRIPTION OF THE DRAWINGS

For a fuller understanding of the nature and objects of the invention, reference should be made to the accompanying drawings and the subsequent description. Briefly, the drawings are.

FURTHER DESCRIPTION OF THE INVENTION

Figure 1:
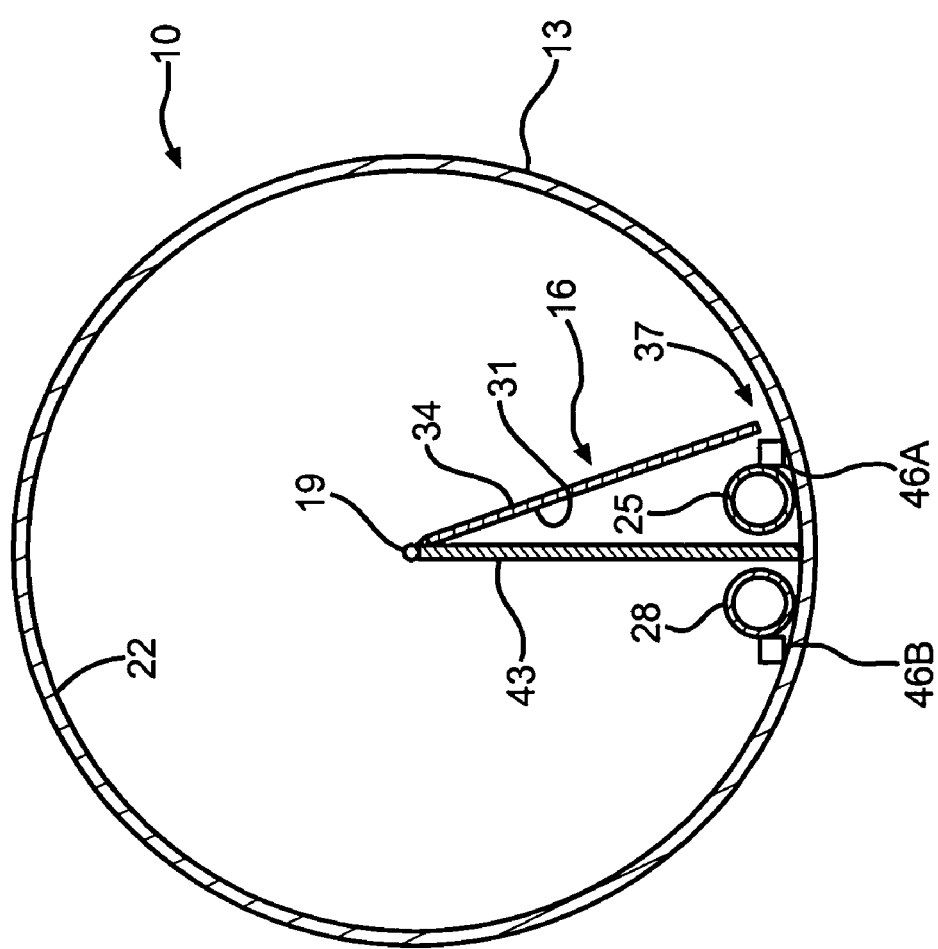
FIG. 1, which is a plan view depicting features of a separator according to the invention.

FIGS. 1 through 4 depict an embodiment of the invention. In FIGS. 1 through 4 there is shown a gas separator 10 that has a housing 13, a movable divider 16 disposed in the housing 13, and a guide 19 disposed in the housing 13. The housing 13 may have an inner surface 22, a first orifice 25 in pneumatic communication with a patient, and a second orifice 28 in pneumatic communication with a supply of gas.

The movable divider 16 may have a first side 31, a second side 34 and an edge 37 between the first and second sides 31, 34. The edge 37 may be positioned proximate to the inner surface 22 of the housing 10 to limit, but not prevent, the movement of gas from the first side 31 to the second side 34, or from the second side 34 to the first side 31. As such, the movable divider 16 may be sized relative to the inner surface 22 so as to permit the movable divider 16 to move back and forth within the housing 10, but also so as to allow some small amount of gas to move around the movable divider 16.

The guide 19 may be associated with the movable divider 16 so as to allow the movable divider 16 to move toward the first orifice 25 during inhalation and toward the second orifice 28 during exhalation. The guide 19 may be associated with the movable divider 16 so as to keep the edge 37 proximate to the inner surface 22 of the housing 13. For example, the guide 19 may extend through the movable divider 16. In one embodiment of the invention, the guide 19 may be a rigid post which is hingedly associated with the movable divider 16 so that the movable divider 16 is allowed to pivot about the post, or the post may pivot within a set of sockets in the housing 13, or both.

The invention may include a stationary divider 43 extending from the inner surface 22 and located between the first orifice 25 and the second orifice 28. In such an arrangement, the guide 19 may be a post which is hingedly associated with the movable divider 16 and the stationary divider 43 so that the movable divider 16 pivots about an end of the stationary divider 43.

In an embodiment of the device depicted in FIGS. 1 through 4, the movable divider 16 may be made from mylar. It is believed this material may be fashioned into a movable divider 16 which provides an appropriate combination of rigidity and mass to allow proper movement of an appropriately sized movable divider 16. Such a movable divider 16 will have a low inertia to allow the movable divider 16 to react quickly to changes in the direction of gas flow through the housing. For example, for a housing 13 having an inner surface with a 50 millimeter radius and a volume of 375 milliliter, an appropriately sized movable divider 16 may be 48 millimeters by 49 millimeters, and 0.3 millimeters thick. In that arrangement, a gap of approximately one millimeter will exist between the edge 37 and the inner surface 22. If the housing 13 has a height of 50 millimeters, a one millimeter gap would exist between the upper surface of the housing 13 and the movable divider 16, as well as a 1 millimeter gap between the lower surface of the housing 13 and the movable divider 16. In total, an area of about 150 square millimeters will exist between the housing 13 and the movable divider 16, which is greater than the cross-sectional area of an adult endotracheal tube. With these features, it is believed the separator 10 may be used to accommodate ventilation of a 40 kilogram patient. These features are merely illustrative of how the invention might be configured.

Figure 2:
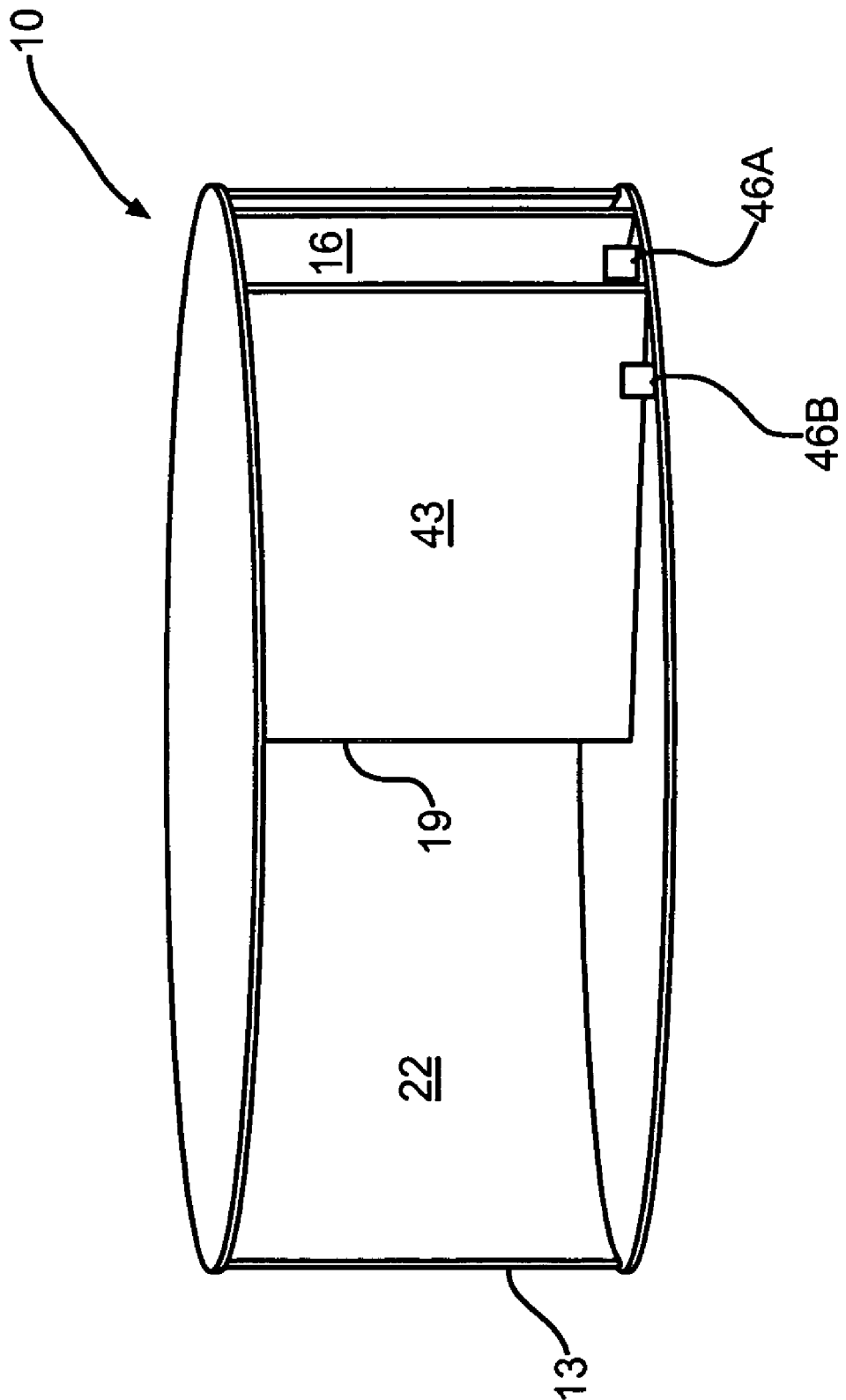
FIG. 2, which is a perspective side view of a separator according to the invention with part of the housing removed to reveal the stationary divider, the movable divider and two bumpers.
Figure 3:
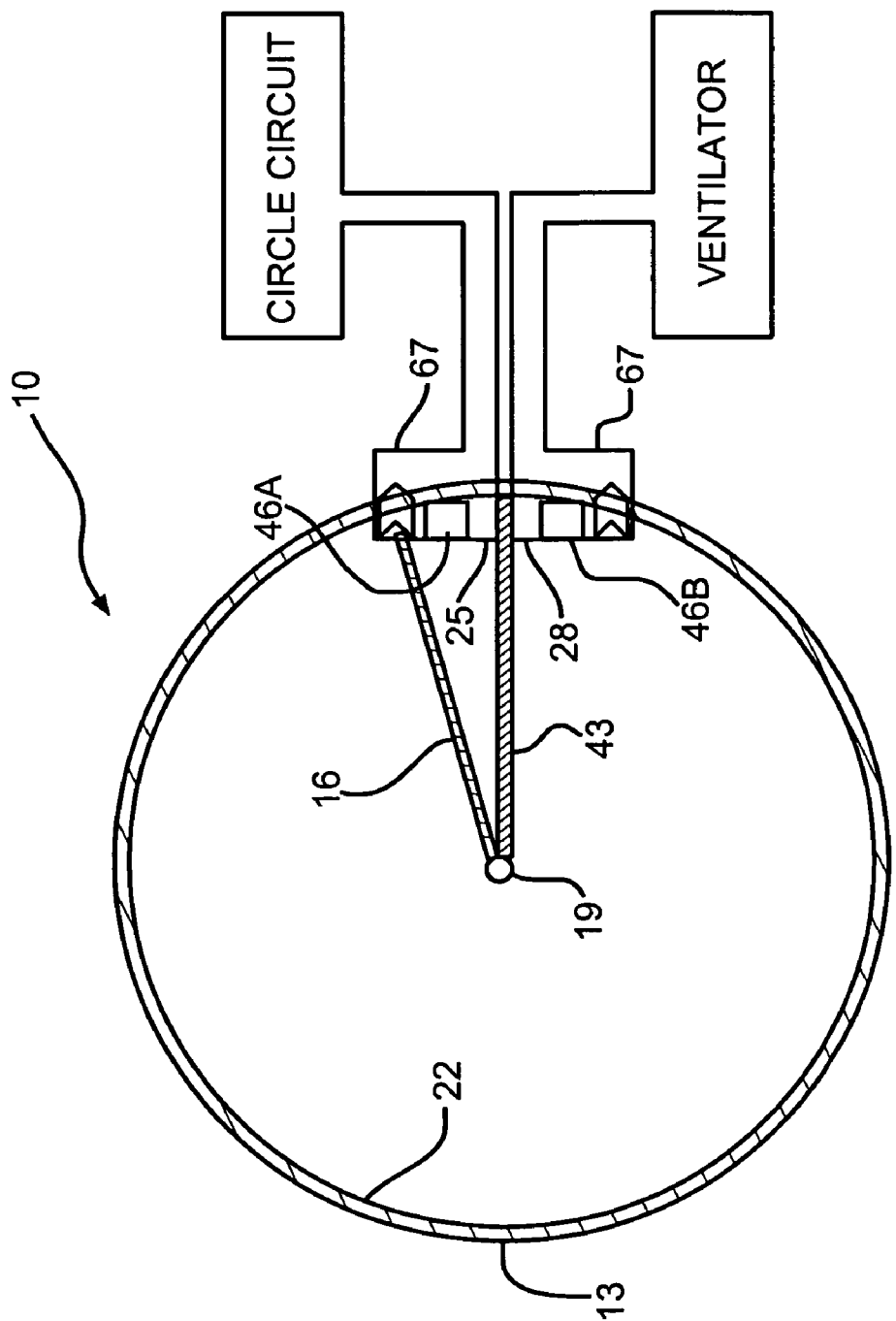
FIG. 3, which is a plan view depicting a separator according to the invention connected to a ventilator and a circle circuit.

The invention may include one or more bumpers 46 in the housing 13. FIGS. 1 through 3 show a first bumper 46A, which may be positioned to limit further movement of the movable divider 16 toward the first orifice 25. When the movable divider 16 is against the bumper 46A, the gap between the movable divider 16 and the housing 13 would allow gas from the second orifice 28 to pass between the edge 37 and the housing 13 before reaching the first orifice 25. In this fashion, gas from the second orifice 28 is not prevented from moving from the second orifice 28 to the first orifice 25.

FIGS. 1 through 3 also show a second bumper 46B, which may be positioned to limit movement of the movable divider 16 toward the second orifice 28. This would force gas from the first orifice 25 to pass between the edge 37 and the housing 13 before reaching the second orifice 28. In this fashion, gas from the first orifice 25 is not prevented from moving from the first orifice 25 to the second orifice 28 when the movable divider 16 is in contact with the bumper 46B.

The movable divider 16 may contact a bumper 46 if there are air leaks from a patient's side of a gas circuit that is in pneumatic communication with the first orifice 25. The movable divider 16 may also contact a bumper 46 if fresh gas flows into the patient's side to maintain rebreathing circuit oxygen concentration, or to deliver therapeutic agent. Another reason the movable divider 16 may contact a bumper 46 is if there are differences between inhaled volume and exhaled volume in a complete respiratory cycle.

The inner surface 22 of the housing 13 may be at least partially arcuate. For example, the inner surface 22 may be cylindrical. As an example of the invention, if the inner surface 22 is a right circular cylinder, the movable divider 16 may be made rectangular and allowed to pivot about a post positioned along the center axis of the cylinder. In this fashion, the edge 37 of the movable divider 16 will remain the same distance from the inner surface 22, no matter what the position of the movable divider 16 is. Other types of cylinders may be used, and the inner surface 22 need not be cylindrical. The housing 13 may have an inner surface 22 that provides an oval cross section, and thereby provide a separator 10 in which the distance between the edge 37 and the inner surface 22 varies with the position of the movable divider 16.

Figure 4:
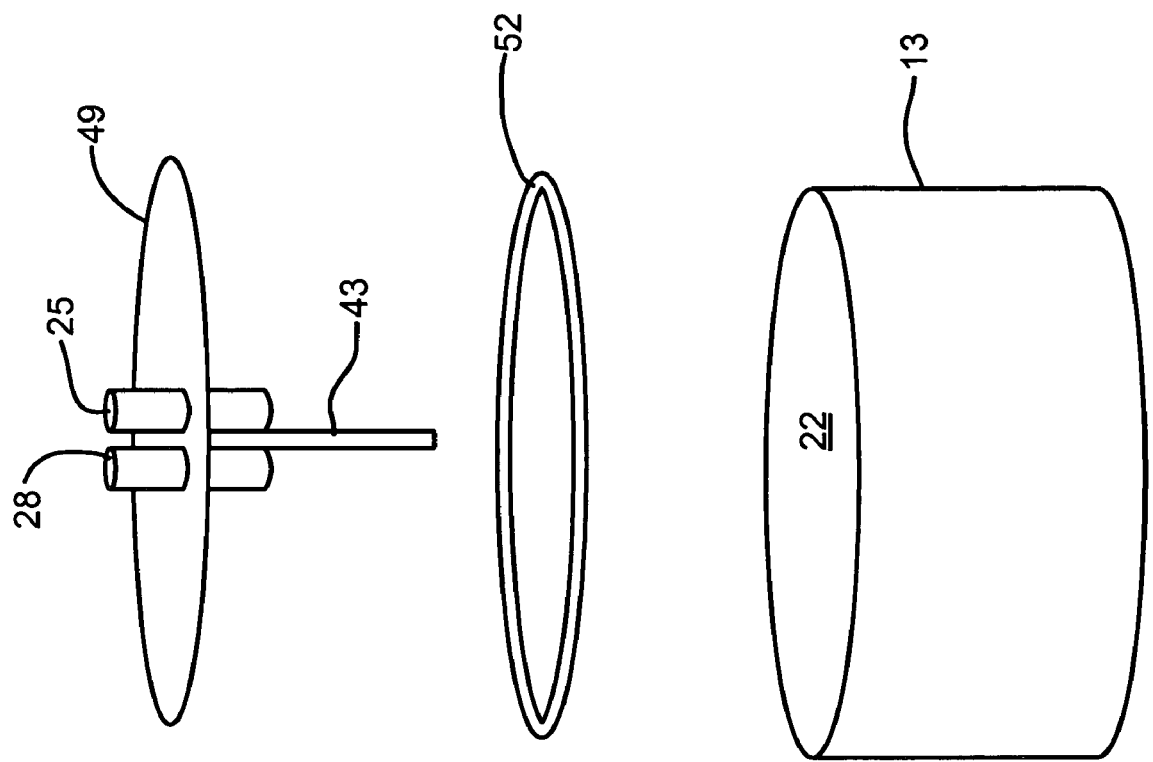
FIG. 4, which is an exploded perspective view of a separator according to the invention.

FIG. 4 shows that the housing 13 may have a removable portion 49. A gasket 52 may be provided to assure a proper seal between the removable portion 49 and the remainder of the housing 13. By providing a removable portion 49, a separator 10 according to the invention may be easily assembled, allow for replacement of worn parts, and allow the separator 10 to be cleaned more easily.

Figure 5:
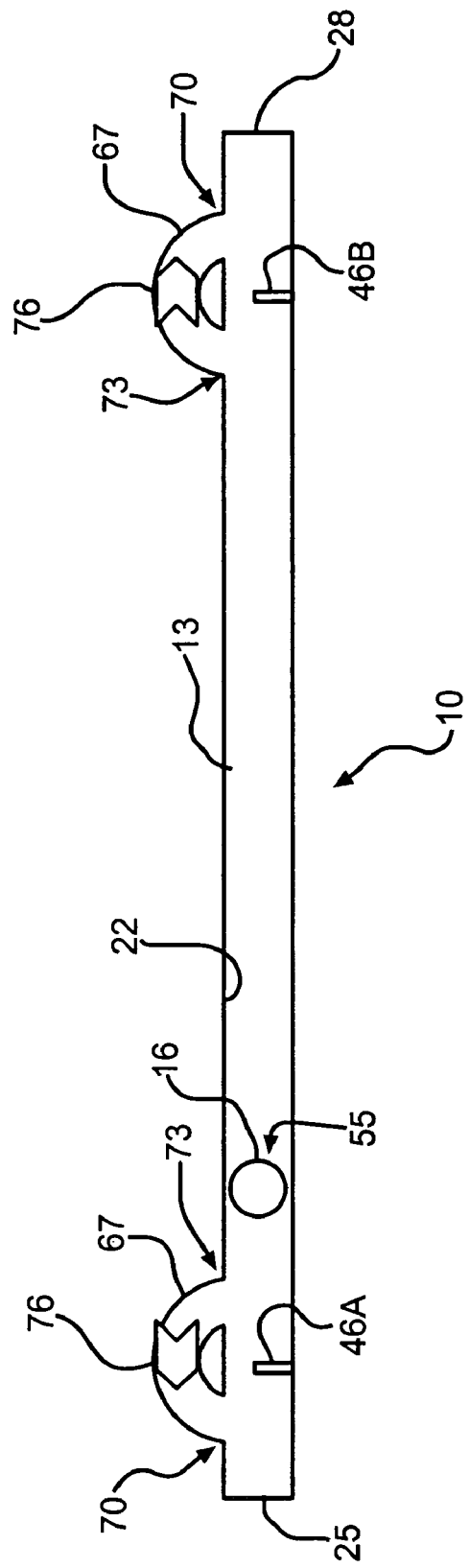
FIG. 5, which is a diagram of a separator according to the invention.

FIG. 5 depicts an embodiment of the invention in which the movable divider 16 is spherical, and instead of having an edge 37, it is more appropriate to refer to the spherical movable divider 16 as having an arcuate surface 55 proximate to the inner surface 22. The separator 10 depicted in FIG. 5 shows an arrangement in which the inner surface 22 is sized relative to the movable divider 16 so that the movable divider 16 is allowed to move toward the first orifice 25 during inhalation and toward the second orifice 28 during exhalation. Since the movable divider 16 is spherical, there may not be a need for the guide 19, and so FIG. 5 does not show a guide 19. However, it should be noted that a guide 19 may be provided to extend through an orifice of a spherical movable divider 16, if desired.

Figure 6:
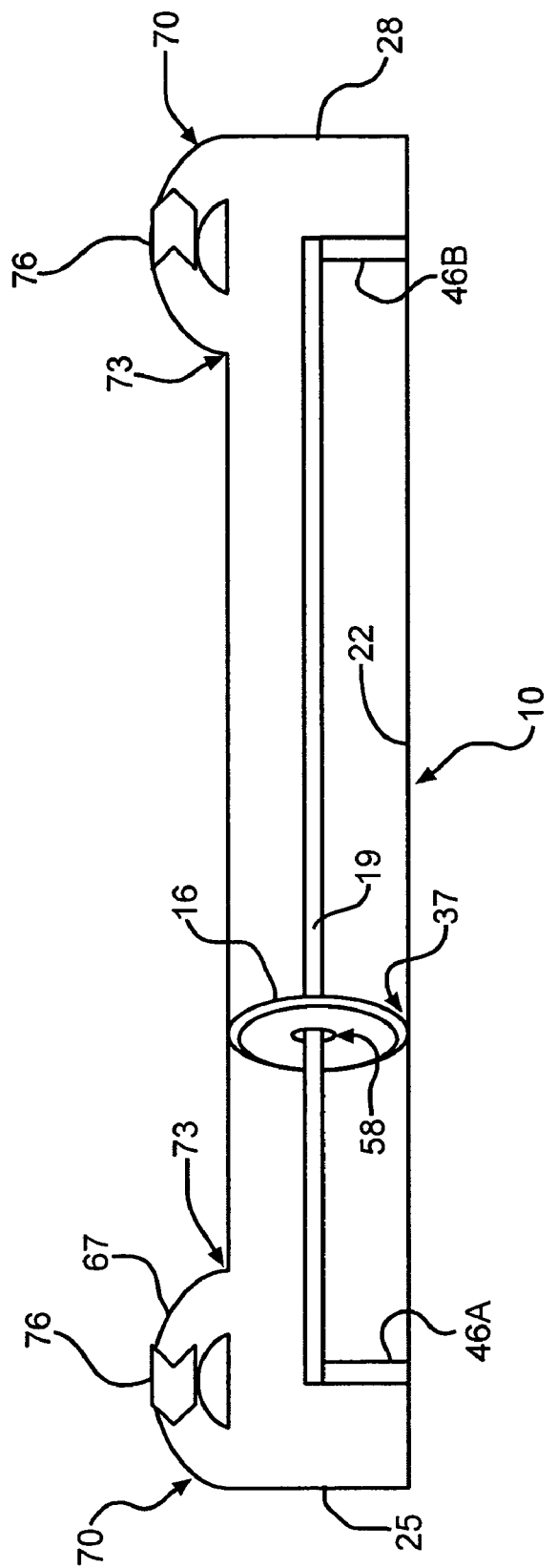
FIG. 6, which is a diagram of a separator according to the invention.
Figure 7:
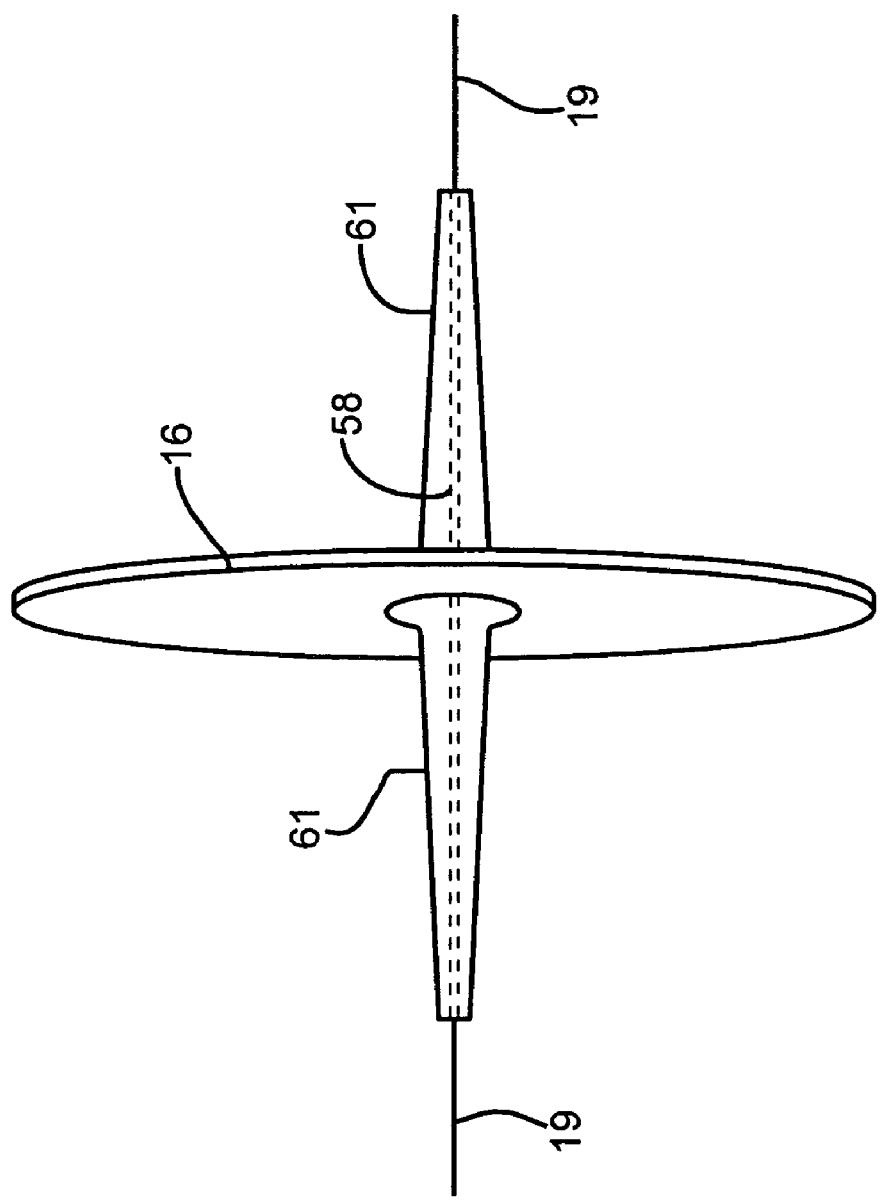
FIG. 7, which is a perspective side view of a disc having a sleeve.
Figure 8:
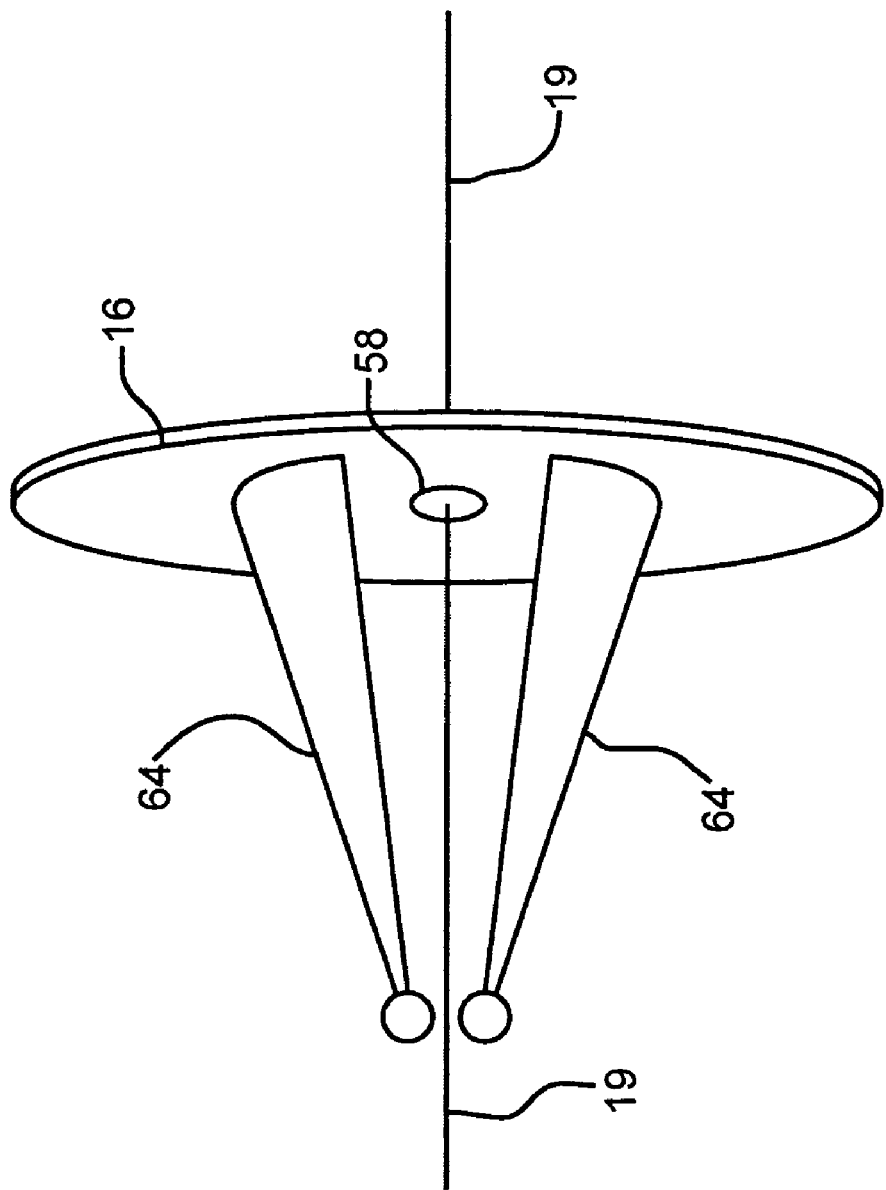
FIG. 8, which is a perspective side view of a disc having struts.

FIG. 6 depicts an embodiment of the invention in which the housing 13 is tubular and the surface of the movable divider 16 that is proximate to the inner surface 22 is an arcuate edge 37. The movable divider 16 is shown as a disc. The disc may include an orifice 58 through which the guide 19 may extend. In FIG. 6, the guide 19 is in the form of a wire. FIG. 7 shows a disc having one or more sleeves 61 to keep the disc oriented substantially perpendicular to the guide 19. For similar results, the disc may include one or more struts 64 connected to the disc and extending toward the guide 19. See FIG. 8. It will be recognized that an arrangement like that shown in FIG. 6 need not use a tubular housing 13—indeed the housing 13 may be any number of shapes and the movable divider 16 may have a correspondingly similar edge 37.

The housing 13 may include one or more bypass lines 67. A bypass line 67 may have a first end 70 and a second end 73, the ends of the bypass line 67 being connected to the housing 13 so that when the edge 37 of the movable divider 16 is between the first and second ends 70, 73, gas is allowed to pass through the bypass line 67. In this fashion, when the movable divider 16 reaches one of the bumpers 46, gas may be allowed to pass by the movable divider 16 via the bypass line 67. A check valve 76 may be provided in the bypass line 67 to assure flow through the bypass line 67 is unidirectional. The bypass line 67 may be provided in order to allow excess inhaled (or exhaled) gas to bypass the movable divider 16, mixing with the other stream of gas, but only when the movable divider 16 abuts a bumper 46.

In another arrangement, the ends 70, 73 of the bypass line 67 may be connected to the housing 13 so that when the edge 37 of the movable divider 16 is aligned with one of the ends 70, 73 of the bypass line 67, gas is allowed to pass through the bypass line 67. In this fashion, utilization of the bypass line 67 may begin even though the edge 37 is not between the ends 70, 73 of the bypass line 67.

Figure 9:
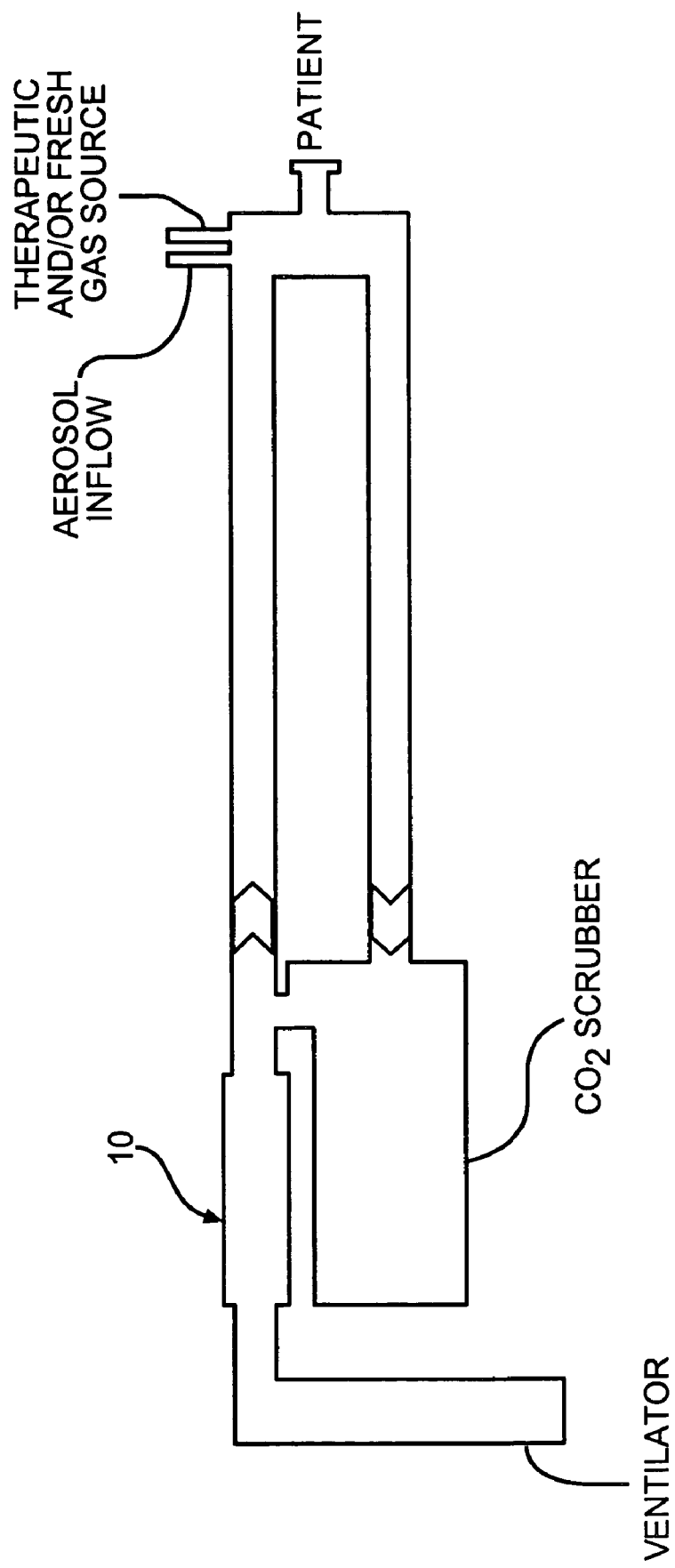
FIG. 9, which is a diagram of a separator according to the invention used in conjunction with a ventilator.
Figure 10:
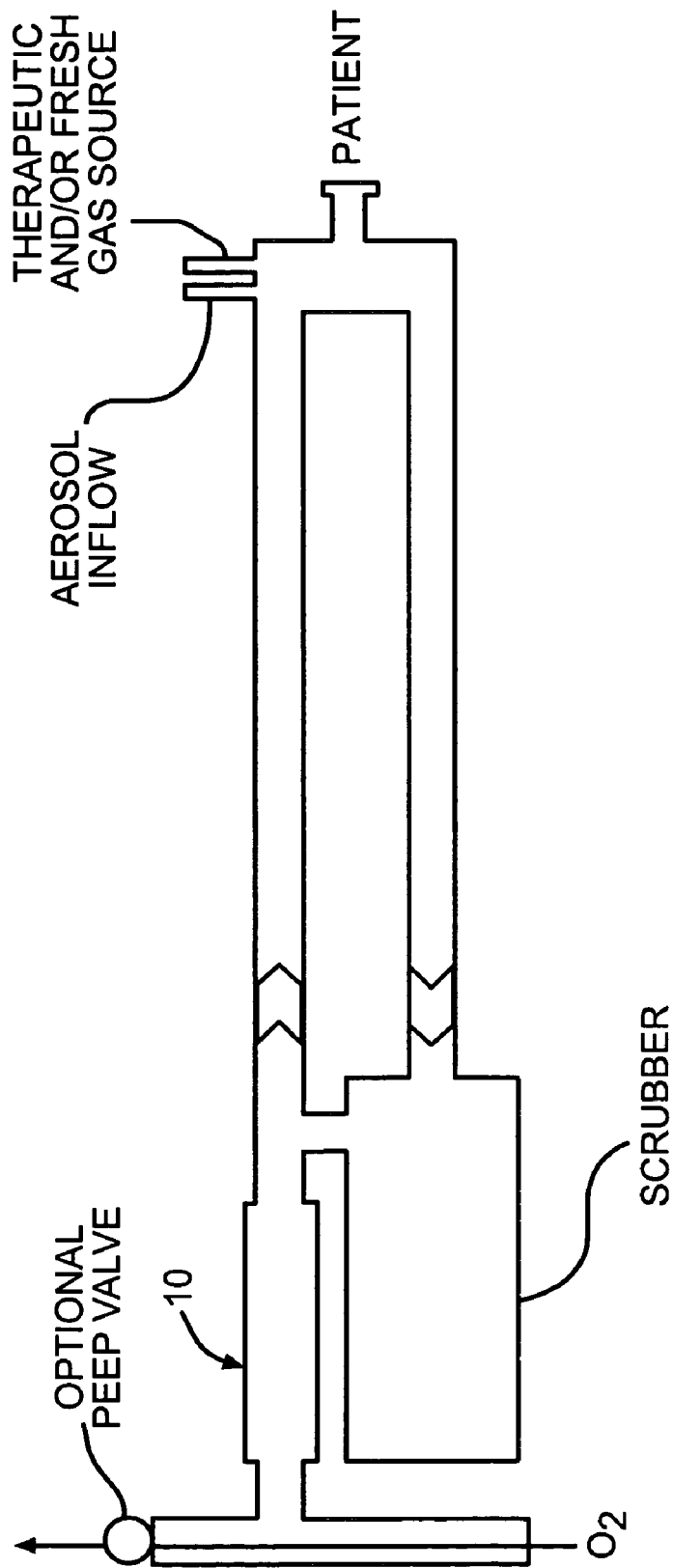
FIG. 10, which is a diagram of a separator according to the invention used in conjunction with a fresh gas source.
Figure 11:
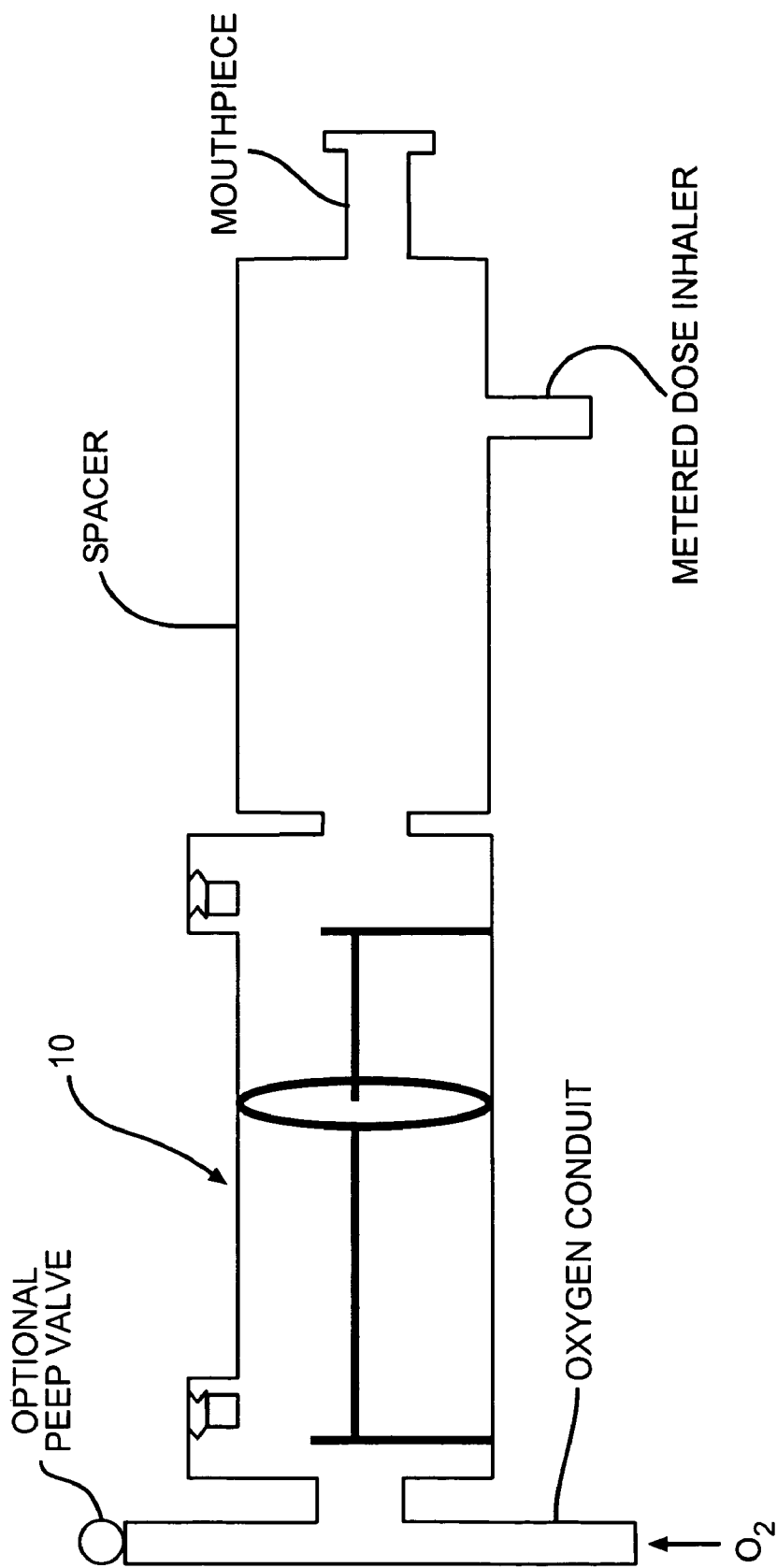
FIG. 11, which is a diagram of a separator according to the invention used in conjunction with a metered dose inhaler.
Figure 12:
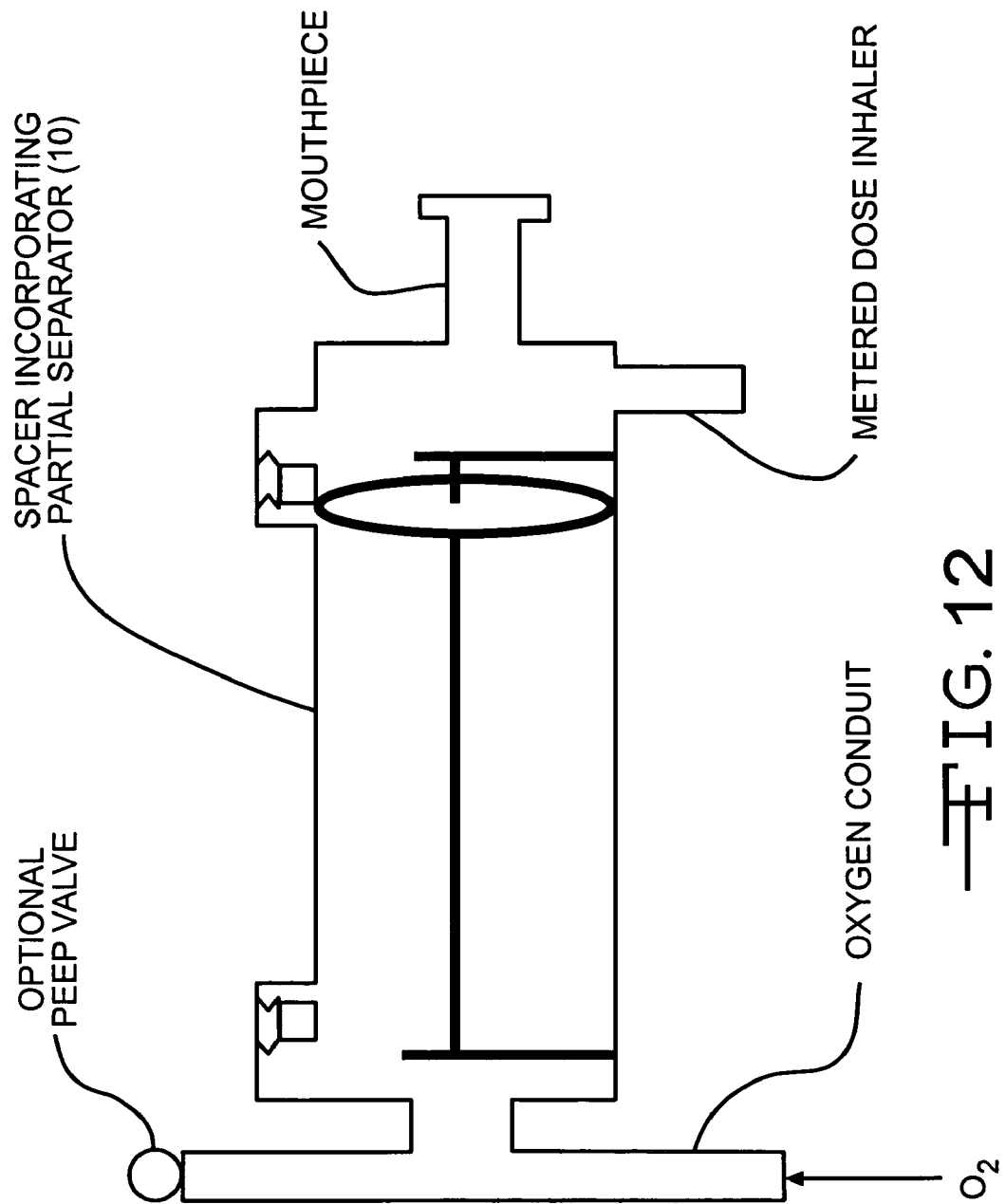
FIG. 12, which is a diagram of a separator according to the invention used in conjunction with a metered dose inhaler, FIG. 13, which shows steps of a method according to the invention.

The invention may be employed in several contexts. For example, the invention may serve to interface between a mechanical ventilator and a rebreathing circuit. The rebreathing circuit may include a $CO_2$ scrubber. See FIG. 9. Another way to employ the invention might be as an interface between a fresh gas source and a rebreathing circuit which includes a $CO_2$ scrubber, during spontaneous breathing See FIG. 10. A further way to employ the invention may be as an interface between a fresh gas source to a patient during spontaneous rebreathing and a spacer for purposes of briefly administering a metered dose inhaler treatment. See FIG. 11. Another way the separator may be employed is to interface between a fresh gas source and a metered dose inhaler. See FIG. 12.

Figure 13:
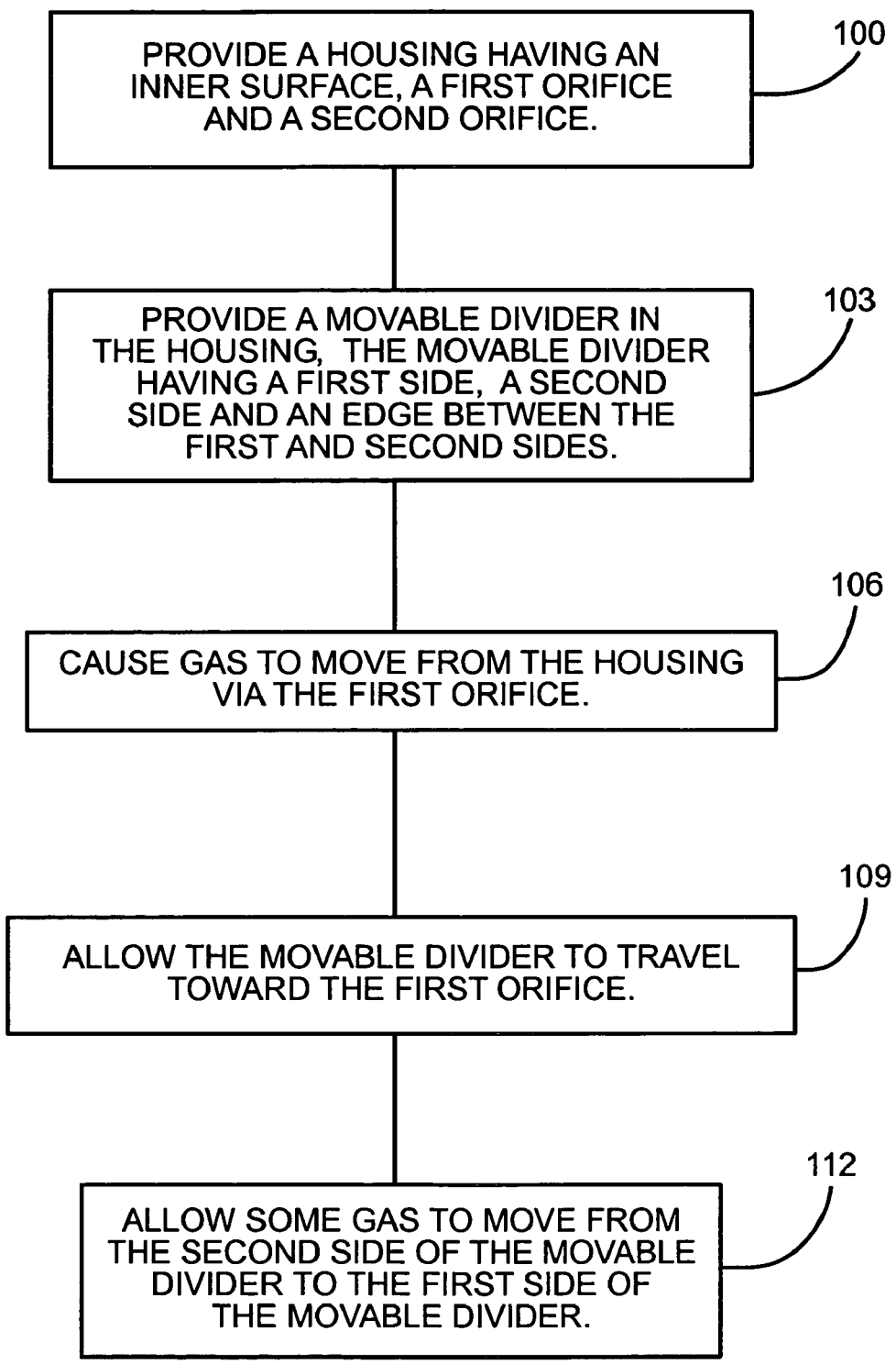

The invention may be embodied as a method of partially separating gas. FIG. 13 shows steps of such a method. In such a method a housing may be provided 100, which has an inner surface, a first orifice in pneumatic communication with a patient, and a second orifice in pneumatic communication with a supply of gas. A movable divider, such as that described above, may be provided 103 in the housing. Gas may be caused 106 to move from the housing via the first orifice. While moving gas from the housing, the movable divider may be allowed 109 to travel toward the first orifice and some gas may be allowed 112 to move from the second side of the movable divider to the first side of the movable divider. Such an operation may be performed during inhalation by a patient. Further, such an operation may be performed while gas is caused to move into the housing via the second orifice.

Figure 14:
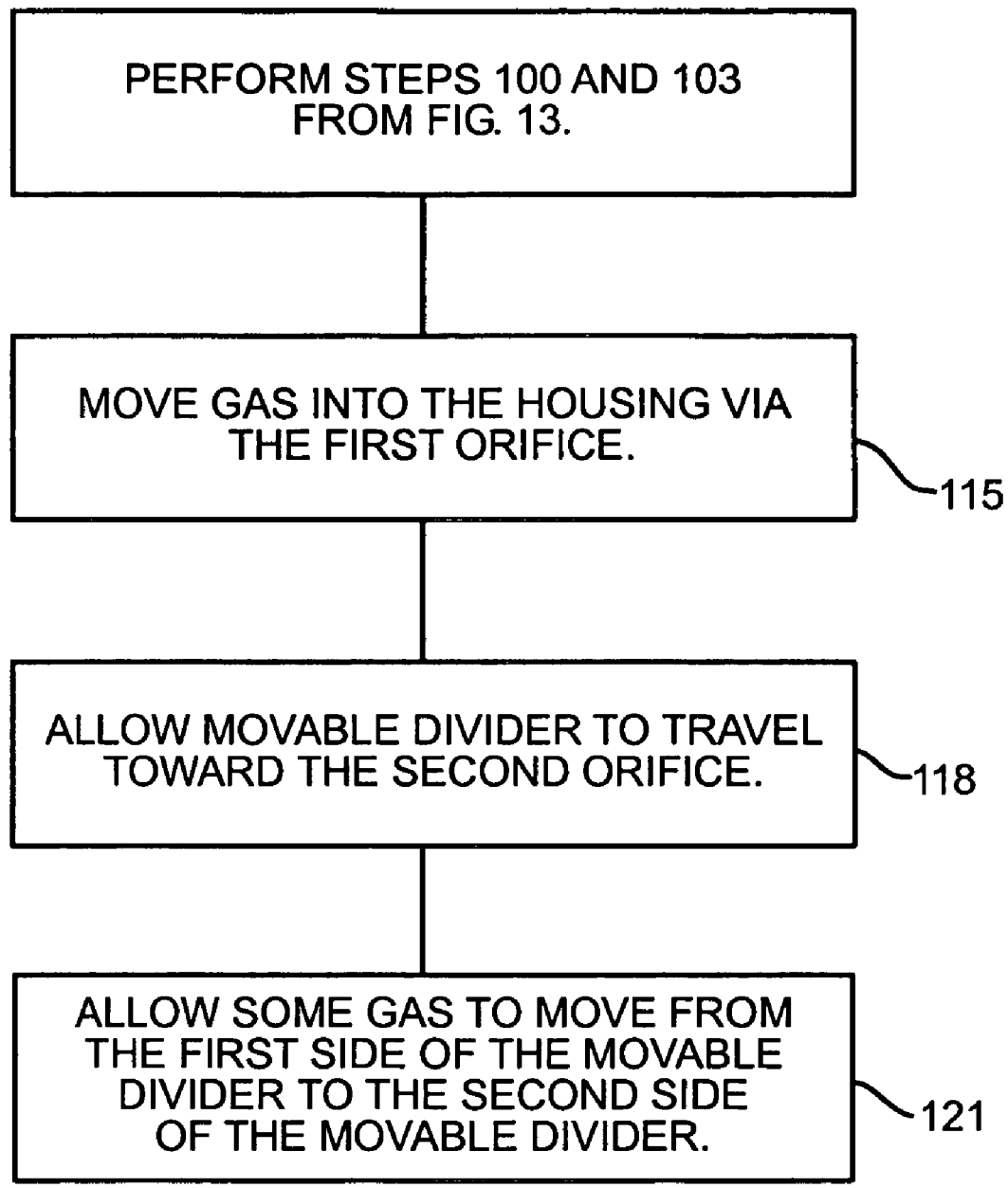
FIG. 14, which shows steps of a method according to the invention.

The method may also be reversed to allow for exhalation by the patient. FIG. 14 shows such a process. For example, gas may be caused to move 115 into the housing via the first orifice. While gas is moving into the housing, the movable divider may be allowed 118 to travel toward the second orifice, and some gas may be allowed 121 to move from the first side of the movable divider to the second side of the movable divider. Further, such an operation may be performed while gas is caused to move from the housing via the second orifice.

The housing may be able to have within it a volume of gas that exceeds the volume of gas in a patient's breath by several fold. For example, a volume of 0.5 liters may accommodate most children between the ages of birth and 10 years.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A gas separator, comprising:
   a housing, having an inner surface, a first orifice in pneumatic communication with a rebreathing device, and a second orifice in pneumatic communication with a supply of fresh gas;
   a movable divider in the housing, the movable divider having a first side, a second side and an edge between the first and second sides, the edge being positioned proximate to the inner surface of the housing to limit, but not prevent, the movement of gas from one of the sides to the other side;
   a guide in the housing, the guide being associated with the movable divider so as to allow the edge to move toward the first orifice during inhalation and toward the second orifice during exhalation, and being associated with the movable divider so as to keep the edge proximate to, and substantially the same distance from, the inner surface of the housing during movement of the edge; and
   a stationary divider extending from the inner surface and located between the first orifice and the second orifice.

2. The separator of claim 1, wherein the guide is a post which is hingedly associated with the movable divider and the stationary divider.

3. The separator of claim 1, wherein the guide is a post which is hingedly associated with the movable divider.

4. The separator of claim 1, further comprising a bumper in the housing, the bumper being positioned to limit motion of the divider and require gas from the first orifice to pass between the edge and the housing before reaching the second orifice.

5. The separator of claim 1, further comprising a bumper in the housing, the bumper being positioned to limit motion of the divider and require gas from the second orifice to pass between the edge and the housing before reaching the first orifice.

6. The separator of claim 1, wherein at least part of the inner surface is arcuate.

7. The separator of claim 6, wherein the inner surface is cylindrical.

8. The separator of claim 6, wherein the movable divider is rectangular.

9. The separator of claim 1, further comprising a bypass line with a first end and a second end, the ends of the bypass line being connected to the housing so that when the edge of the movable divider is between the first and second ends, gas is allowed to pass through the bypass line.

10. The separator of claim 9, further comprising a check valve in the bypass line.

11. The separator of claim 1, further comprising a bypass line with a first end and a second end, the ends of the bypass line being connected to the housing so that when the edge of the movable divider is aligned with one of the ends of the bypass line, gas is allowed to pass through the bypass line.

12. The separator of claim 11, further comprising a check valve in the bypass line.

13. A gas separator, comprising:
   a housing, having an inner surface, a first orifice in pneumatic communication with a rebreathing device, and a second orifice in pneumatic communication with a supply of fresh gas; and a movable divider in the housing, the movable divider having an edge surface positioned proximate to the inner surface of the housing during movement of the edge surface to limit, but not prevent, the movement of gas past the movable divider, and the movable divider is sized relative to the inner surface so as to allow the edge surface to move toward the first orifice during inhalation and toward the second orifice during exhalation wherein the distance from the edge surface to the inner surface of the housing is substantially the same throughout the movement of the edge surface.

14. The separator of claim 13, further comprising a bumper in the housing, the bumper being positioned to limit motion of the divider and require gas from the first orifice to pass between the edge surface and the housing before reaching the second orifice.

15. The separator of claim 13, further comprising a bumper in the housing, the bumper being positioned to limit motion of the divider and require gas from the second orifice to pass between the edge surface and the housing before reaching the first orifice.

16. A method of partially separating gas, comprising:
providing a housing, having an inner surface, a first orifice in pneumatic communication with a rebreathing device, and a second orifice in pneumatic communication with a supply of fresh gas;
providing a movable divider in the housing, the movable divider having a first side, a second side and an edge between the first and second sides, the edge being positioned proximate to the inner surface of the housing during movement of the edge to limit, but not prevent, the movement of gas from one of the sides to the other side, and wherein the distance from the edge to the inner surface of the housing is substantially the same throughout the movement of the edge; and
moving gas from the housing, and allowing the edge to travel toward the first orifice, and allowing some gas to move from the second side to the first side.

17. The method of claim 16, further comprising moving gas into the housing, and allowing the movable divider to travel toward the second orifice, and allowing some gas to move from the first side to the second side.

18. The method of claim 16, further comprising providing a therapeutic agent in pneumatic communication with the patient.

19. The method of claim 16, wherein the first orifice is in pneumatic communication with a supply of fresh gas.

* * * * *